United States Patent
Henderson

(10) Patent No.: US 9,132,286 B2
(45) Date of Patent: *Sep. 15, 2015

(54) INCLINED BEAMLINE MOTION MECHANISM

(71) Applicant: Toby D. Henderson, Rockford, IL (US)

(72) Inventor: Toby D. Henderson, Rockford, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/276,373

(22) Filed: May 13, 2014

(65) Prior Publication Data

US 2014/0243582 A1    Aug. 28, 2014

Related U.S. Application Data

(63) Continuation of application No. 13/760,612, filed on Feb. 6, 2013, now Pat. No. 8,757,877, which is a continuation of application No. 12/262,992, filed on Oct. 31, 2008, now Pat. No. 8,394,007.

(51) Int. Cl.
*A61N 5/10* (2006.01)

(52) U.S. Cl.
CPC ............... *A61N 5/1081* (2013.01); *A61N 5/10* (2013.01); *A61N 2005/1087* (2013.01)

(58) Field of Classification Search
CPC ............ A61N 5/00; A61N 5/01; A61N 5/10; A61N 5/1042–5/1045; A61N 5/1047; A61N 5/1077; A61N 5/1081; A61N 5/1082; G21K 1/00; G21K 1/02; G21K 1/025; H05H 7/001; H05H 2007/002
USPC .................................. 600/1–8; 378/197–198
See application file for complete search history.

(56) References Cited

U.S. PATENT DOCUMENTS

| | | | |
|---|---|---|---|
| 1,431,578 | A | 10/1922 | Garretson |
| 5,046,495 | A | 9/1991 | Takahashi et al. |
| 5,321,271 | A | 6/1994 | Schonberg et al. |
| 5,540,649 | A | 7/1996 | Bonnell et al. |
| 5,548,625 | A | 8/1996 | Waldo, III |
| 5,577,094 | A | 11/1996 | Fudamoto |
| 5,727,554 | A | 3/1998 | Kalend et al. |
| 5,784,431 | A | 7/1998 | Kalend et al. |
| 6,203,196 | B1 | 3/2001 | Meyer et al. |
| 6,811,313 | B2 | 11/2004 | Graumann et al. |

(Continued)

FOREIGN PATENT DOCUMENTS

| | | | |
|---|---|---|---|
| EP | 1 402 923 A1 | | 3/2004 |
| EP | 1 958 664 A2 | | 8/2008 |

(Continued)

*Primary Examiner* — Charles A Marmor, II
*Assistant Examiner* — Carrie R Dorna
(74) *Attorney, Agent, or Firm* — Reinhart Boerner Van Deuren P.C.

(57) ABSTRACT

A radiotherapy particle emitter positioning device is provided. The positioning device includes first and second arcuate support frames, a mounting carriage and a drive arrangement. The first and second arcuate support frames each include a drive track arrangement defining an arcuate carriage guide path. The mounting carriage is configured for supporting the radiotherapy particle emitter. The mounting carriage is mounted to and supported by the support frames. The mounting carriage is connectable to the drive track arrangements and moveable along the carriage guide path. The mounting carriage also includes the drive arrangement. The drive arrangement engages the drive track arrangements for driving the mounting carriage along the drive track arrangements and the carriage guide path.

5 Claims, 8 Drawing Sheets

(56) References Cited

U.S. PATENT DOCUMENTS

| | | |
|---|---|---|
| 6,869,217 B2 | 3/2005 | Rasche et al. |
| 7,014,361 B1 | 3/2006 | Ein-Gal |
| 7,154,991 B2 | 12/2006 | Earnst et al. |
| 8,394,007 B2 | 3/2013 | Henderson |
| 8,757,877 B2 | 6/2014 | Henderson |
| 2004/0184579 A1 | 9/2004 | Mihara et al. |
| 2005/0194540 A1 | 9/2005 | Fenster et al. |
| 2005/0234327 A1 | 10/2005 | Saracen et al. |
| 2006/0050847 A1 | 3/2006 | Jaffray et al. |
| 2007/0121790 A1 | 5/2007 | Grady |
| 2007/0230660 A1 | 10/2007 | Herrmann |
| 2008/0093567 A1 | 4/2008 | Gall |
| 2009/0070936 A1 | 3/2009 | Henderson et al. |
| 2009/0074151 A1 | 3/2009 | Henderson et al. |

FOREIGN PATENT DOCUMENTS

| | | |
|---|---|---|
| EP | 2 363 171 A1 | 9/2011 |
| JP | 2008-2000092 A | 9/2008 |
| KR | 1020060135063 A | 12/2006 |
| KR | 100695468 B1 | 3/2007 |

INCLINED BEAMLINE MOTION MECHANISM

CROSS-REFERENCE TO RELATED PATENT APPLICATIONS

This patent application is a Continuation application of co-pending U.S. patent application Ser. No. 13/760,612, filed Feb. 6, 2013, which is a Continuation application of U.S. patent application Ser. No. 12/262,992, filed Oct. 31, 2008, which is now issued as U.S. Pat. No. 8,394,007, the entire teachings and disclosure of which are incorporated herein by reference thereto.

FIELD OF THE INVENTION

This invention generally relates to radiotherapy systems and more particularly for positioning systems for positioning proton beam nozzles.

BACKGROUND OF THE INVENTION

In radiotherapy using heavy ions, tumors are bombarded with accelerated particles. A particle accelerator forms and emits a particle beam, typically a proton beam from a proton beam nozzle. During the treatment, the proton beam must be accurately directed at the tumor. Depending on the position of the tumor in the body, different irradiation positions (fields) are provided for the patient. One system for positioning patients during radiotherapy is provided for in U.S. patent application Ser. No. 12/208,807 filed on Sep. 11, 2008, having U.S. Publication No. 2009-0070936, entitled "Patient Positioner System."

While that system provides for significantly improved positioning of the patient within the room in which the radiotherapy by providing different angles as well as an increased positioning envelope, the actual angle at which the proton beam is emitted and directed toward the patient may need to be adjusted. For instance, it may be desirable to allow a patient to lie on his or her back and administer the proton beam in a horizontal direction. However, in another treatment session, it may be desirable to again low the patient to lay on his or her back but to administer the proton beam along an axis that is oblique to the horizontal plane, such as by an angle of about sixty degrees. The different angles may be desired depending on the location of the tumor and the best path to avoid damaging cells that are not part of the tumor.

As such, while being able to adjust the position of the patient is desirable, it is also desirable to adjust the position of the proton beam nozzle and therefore the axis along which the proton beam is administered.

In the past, very large scale structures were used to mount and position the proton beam nozzle. These structures would require very large buildings and rooms for performing the radiotherapy. The present invention relates to improvements in radiotherapy systems and particularly positioning of proton beams in radiotherapy systems.

BRIEF SUMMARY OF THE INVENTION

Embodiments of the invention provide an improved positioning device for supporting and positioning a radiotherapy particle emitter. The positioning device allows an attached particle emitter to have varied axes along which emitted particles may travel during radio therapy treatment. The improved positioning device significantly reduces the footprint that is taken up by the positioning device and consequently the entire radiotherapy system as a whole.

In one form of the invention, the positioning device includes first and second arcuate support frames, a mounting carriage and a drive arrangement. The first and second arcuate support frames each include a drive track arrangement defining an arcuate carriage guide path. The mounting carriage is configured for supporting the radiotherapy particle emitter. The mounting carriage is mounted to and supported by the support frames. The mounting carriage is connectable to the drive track arrangements and moveable along the carriage guide path. The mounting carriage also includes the drive arrangement. The drive arrangement engages the drive track arrangements for driving the mounting carriage along the drive track arrangements and the carriage guide path.

The first drive track arrangement may include a first gear rack arrangement and the second drive track arrangement includes a second gear rack while the drive arrangement includes an at least two point drive arrangement including a first pinion gear engaging the first gear rack arrangement and a second pinion gear engaging the second gear rack arrangement. This provides balanced driving of the mounting carriage and prevents unnecessary torquing of the frame of the mounting carriage.

The positioning device, and particularly the drive track arrangements, may include cam tracks for precision guidance of the mounting carriage along the carriage guide path. The cam tracks may include upper and a lower cam surfaces in opposed facing relation that interact with/cooperate with a plurality of corresponding cam followers.

In yet another aspect, embodiments of the invention include an independent braking system. The independent braking system being independent from the drive arrangement. The braking system may include a two point contact system including pinion gears engaging the gear rack arrangements. The independent braking system having a free state in which the mounting carriage is permitted to move along the carriage guide path and a braking state in which the mounting carriage is prevented from moving along the carriage guide path. This independent braking system can be used during radiotherapy treatments to maintain the position of an attached proton beam nozzle.

Embodiments of the present invention may also include a "fail safe" locking system, also referred to as a secondary braking system, that automatically locks the mounting carriage in the event of control or primary braking failure of the mounting carriage. The fail safe locking system can include shot pin locks, preferably spring loaded shot pin locks, that selectively cooperate with locking aperture arrays, typically including angularly spaced apart apertures and/or cavities, to provide a positive lock preventing movement of the mounting carriage along the carriage guide path.

Further embodiments of the present invention may also include carriage stops for precisely locating the mounting carriage in generally predetermined positions. These carriage stops may include one or more fine adjustment systems for selectively fine calibrating the predetermined positions.

The fine adjustment systems may include fine adjustment bumpers against which the mounting carriage abuts when positioned in the predetermined positions. Alignment systems may also be provided to confirm alignment of the mounting carriage, and consequently an attached particle emitter. Each alignment system includes a cooperating alignment target for receiving an alignment quill.

In one embodiment of the present invention, the drive arrangement is carried by the mounting carriage and moves along the guide path as the mounting carriage moves along the guide path.

Beyond the cam rollers for allowing reduced friction movement along the carriage guide path identified previously, embodiments of the invention may include lateral cam rollers. The lateral cam rollers ride on lateral faces of the cam tracks that face inward toward one another. These later cam rollers facilitate maintaining precise lateral positioning of the mounting carriage relative to the support frames. These lateral cam rollers are preferably adjustable to permit fine tuning or calibrating of the lateral position of the mounting carriage relative to the support frames.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
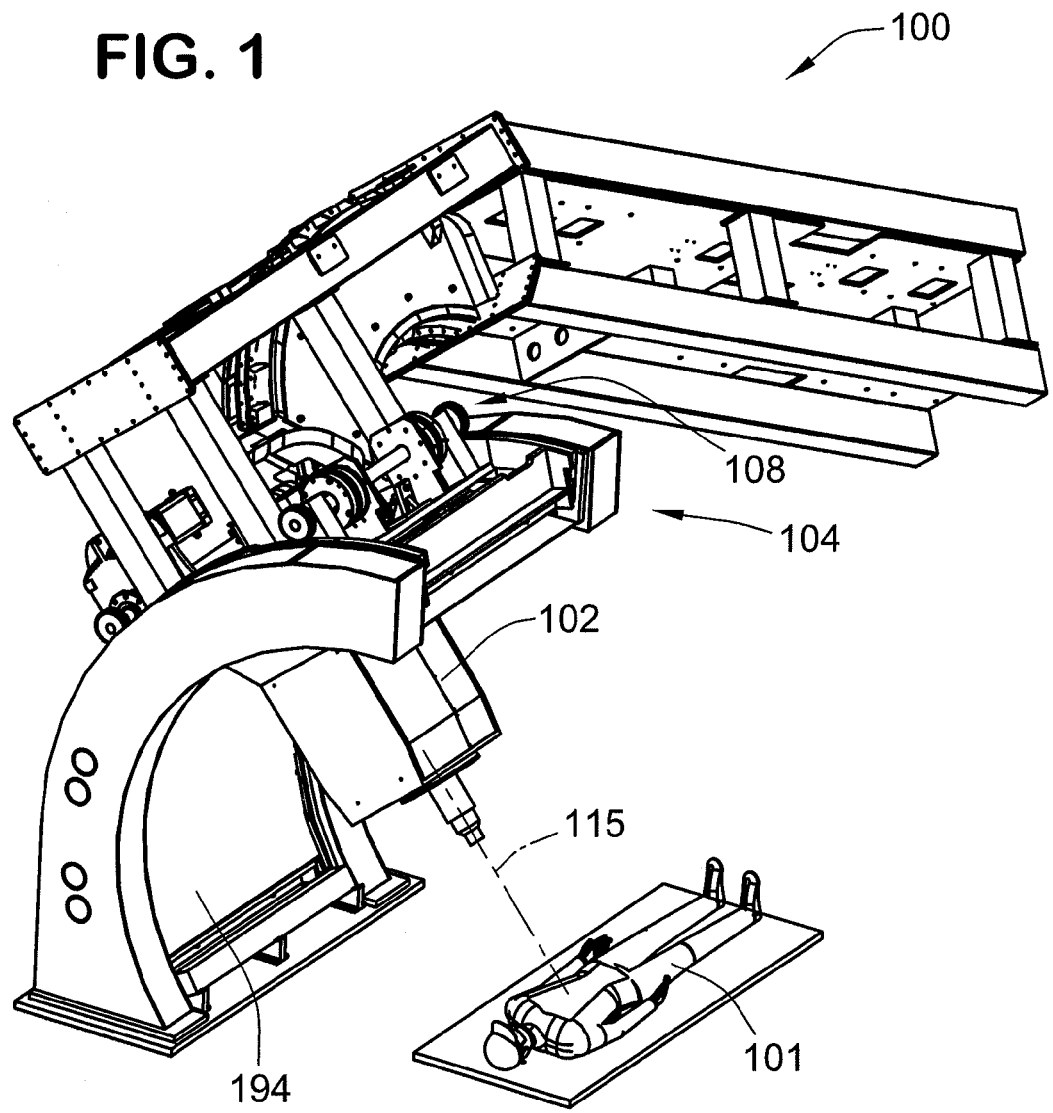
FIG. 1 is a top isometric illustration of a radiotherapy treatment system according to the teachings of the present invention.

FIG. 1 illustrates a first embodiment of a radiotherapy treatment system 100 for performing radiotherapy treatment on a patient 101. The radiotherapy treatment system 100 includes a proton beam nozzle 102, which is a radiotherapy particle emitter for producing and emitting a proton beam to effectuate the radiotherapy treatment. The radiotherapy treatment system 100 also includes a high precision positioning system 104 for positioning the proton beam nozzle 102.

Figure 2:
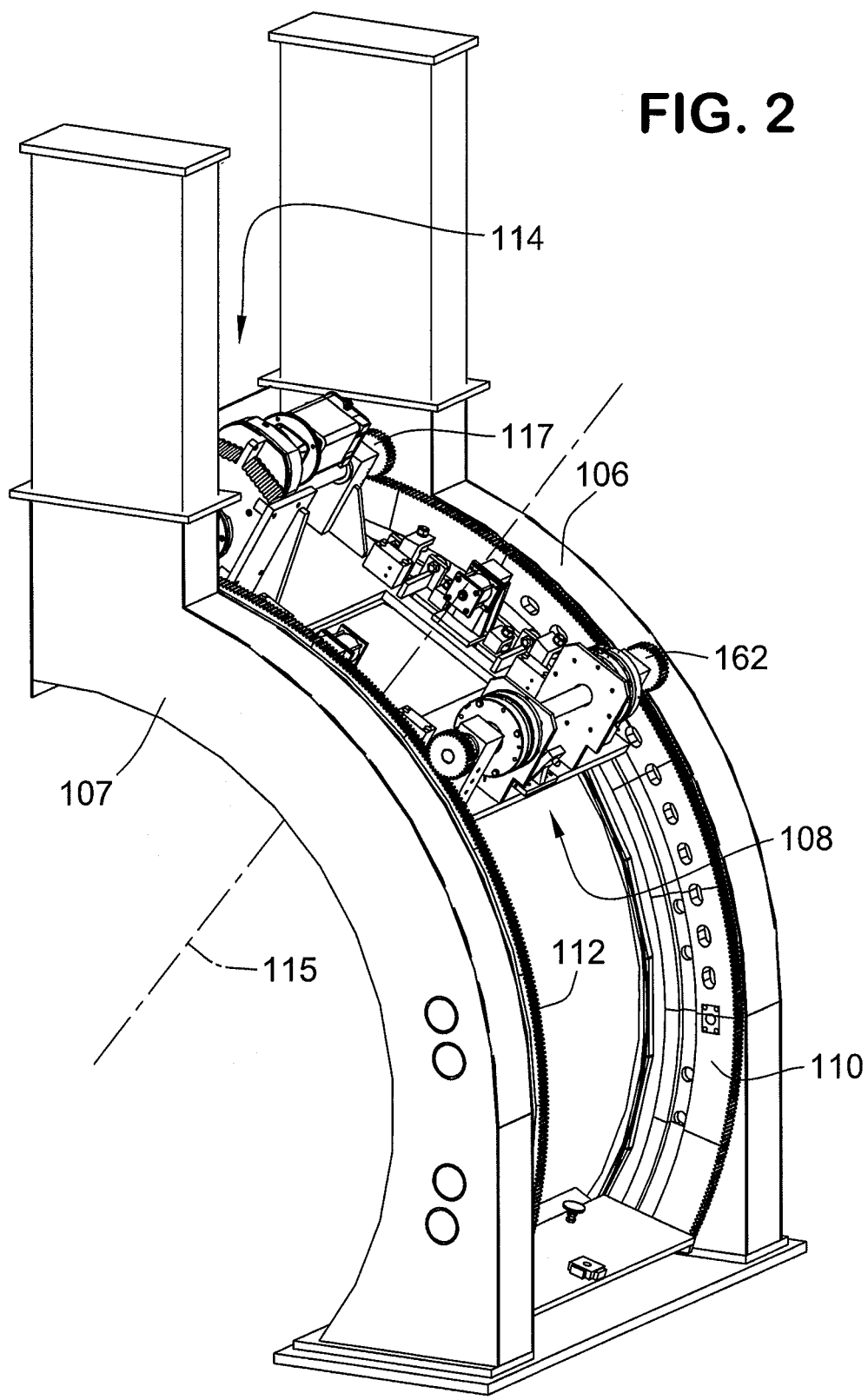
FIG. 2 is a top isometric illustration of the positioning system for the radiotherapy treatment system of FIG. 1.

With reference to FIG. 2, the positioning system 104 generally includes a pair of arcuate support frames 106, 107 upon which a mounting carriage 108 is supported. The mounting carriage 108 is operably coupled to a controller 109 for controlling one or more of its operation, movement and braking about the support frames 106, 107. Each of the support frames 106 are mounted to floor 145 (see FIG. 3).

Each support frame includes a drive track arrangement 110. The drive track arrangements 110, 112 are generally arcuate and substantially mirrored opposites of one another. The drive track arrangements 110, 112 define an arcuate carriage guide path 113 (see e.g. FIG. 3) along which the mounting carriage 108 may be driven to adjust a proton beam axis 115 (see FIG. 1) of the proton beam nozzle 102.

Figure 4:
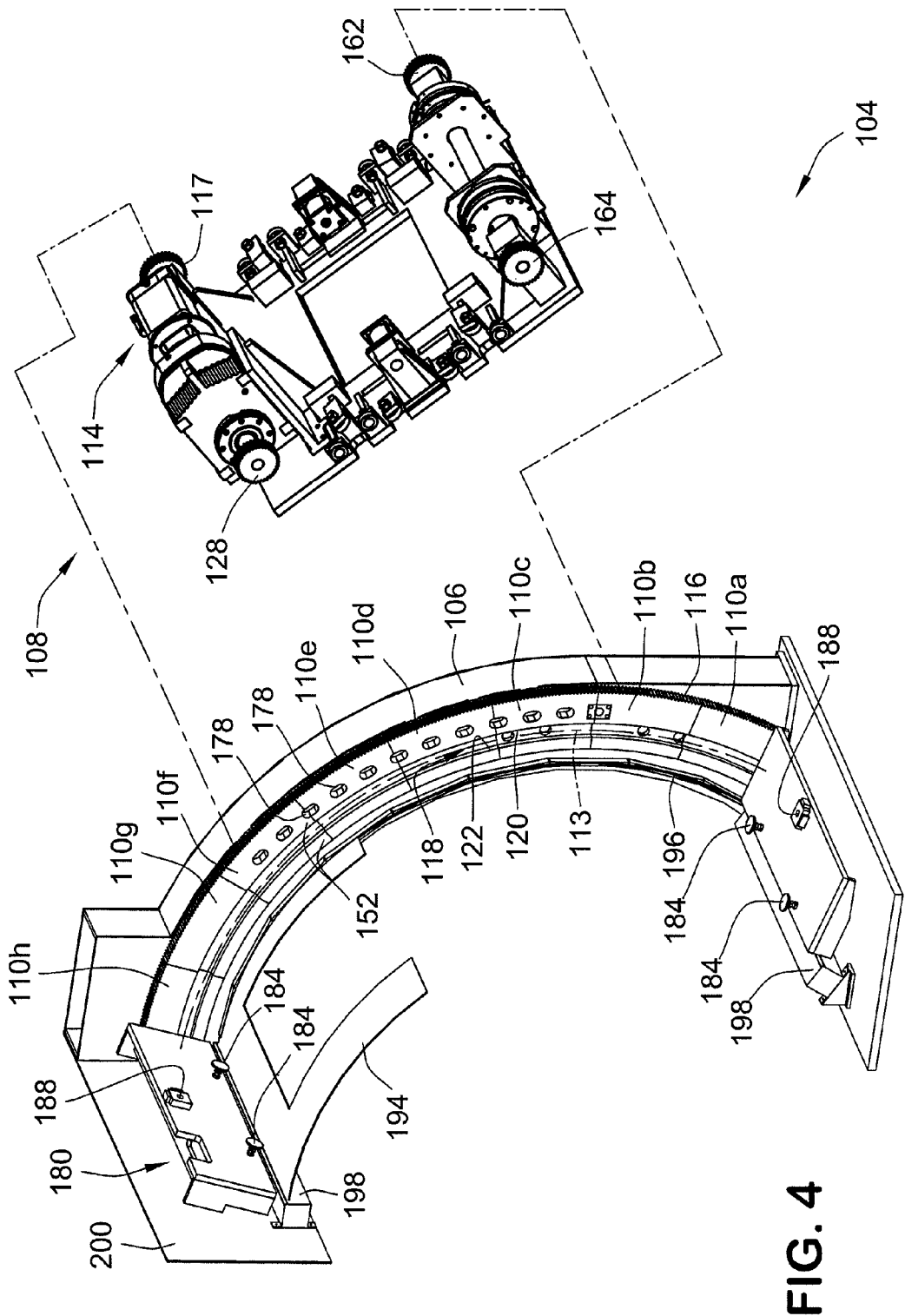
FIG. 4 is a partial side isometric view of the positioning system of FIG. 2 being partially exploded with the carriage removed from the support frames.

As illustrated in FIGS. 2 and 4, the mounting carriage 108 is supported by the support frames 106, 107 and operably connected to the drive track arrangements 110, 112. The mounting carriage 108 includes a drive arrangement 114 operably engaging the drive track arrangements 110, 112 for driving the mounting carriage 108 along the drive track arrangements 110, 112, and consequently the carriage guide path 113 that they define.

The drive track arrangements 110, 112 will be described with reference to FIG. 4. FIG. 4 is a partial exploded illustration of the positioning system 104 and only includes drive track arrangement 110 and support frame 106. However, as the two drive track arrangements 110, 112 are substantially identical, except for being mirrored opposites, the description of guide track 110 will be equally applicable to guide track 112.

Drive track arrangement 110 is generally formed from a plurality of drive track segments 110a-110h. The segments are operably mounted to support frame 106.

The drive track arrangement 110 defines a gear rack 116 that is engaged by the drive arrangement 114 to drive the mounting carriage 108 along the carriage guide path 113. The gear rack 116 faces radially outward to be engaged by a corresponding pinion gear 117 of the drive arrangement 114. In the illustrated embodiment, each segment 110a-110h defines, at least in part, a section of a gear rack 116.

The drive track arrangement 110 further defines a cam track 118 that includes upper and lower cam surfaces 120, 122. The upper and lower cam surfaces 120, 122 are in opposed facing relation and are generally parallel to one another. The cam track 118 generally defines the carriage guide path 113 and is operably interacted with by the mounting carriage to maintain and provide precise predetermined positioning of the mounting carriage, and consequently an attached proton beam nozzle 102. Again, each drive track segment 110a-110h, defines part of the cam track 118.

Figure 3:
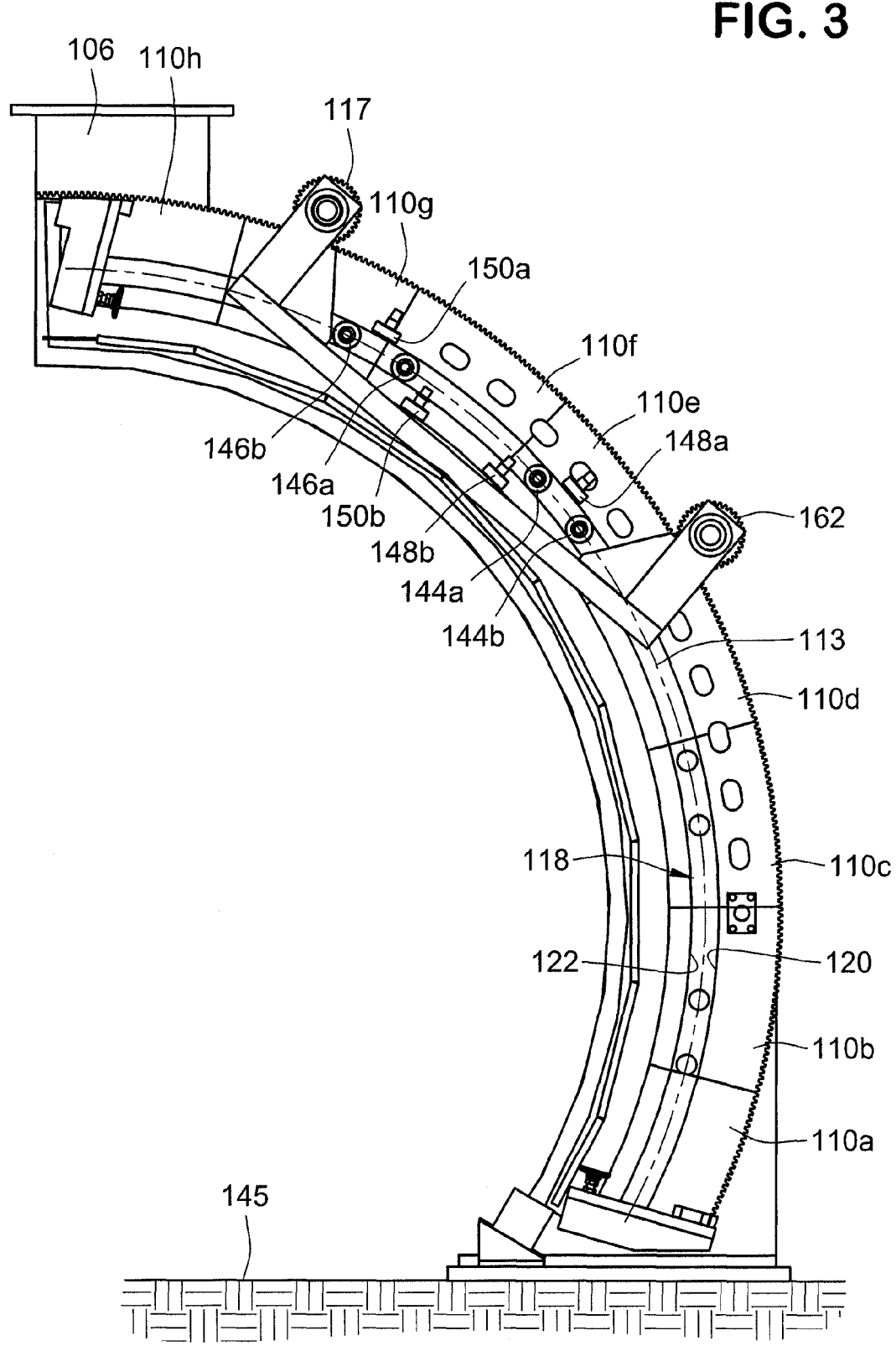
FIG. 3 is a partial side view of the positioning system of FIG. 2.

Thus, in one embodiment, a plurality of the drive track segments 110a-110h are one-piece constructions and each integrally form a portion of the cam track 118 and a portion of the gear rack 116. Additionally, as illustrated in FIG. 3, the gear rack 116 is spaced radially outward from the cam track 118.

Figure 5:
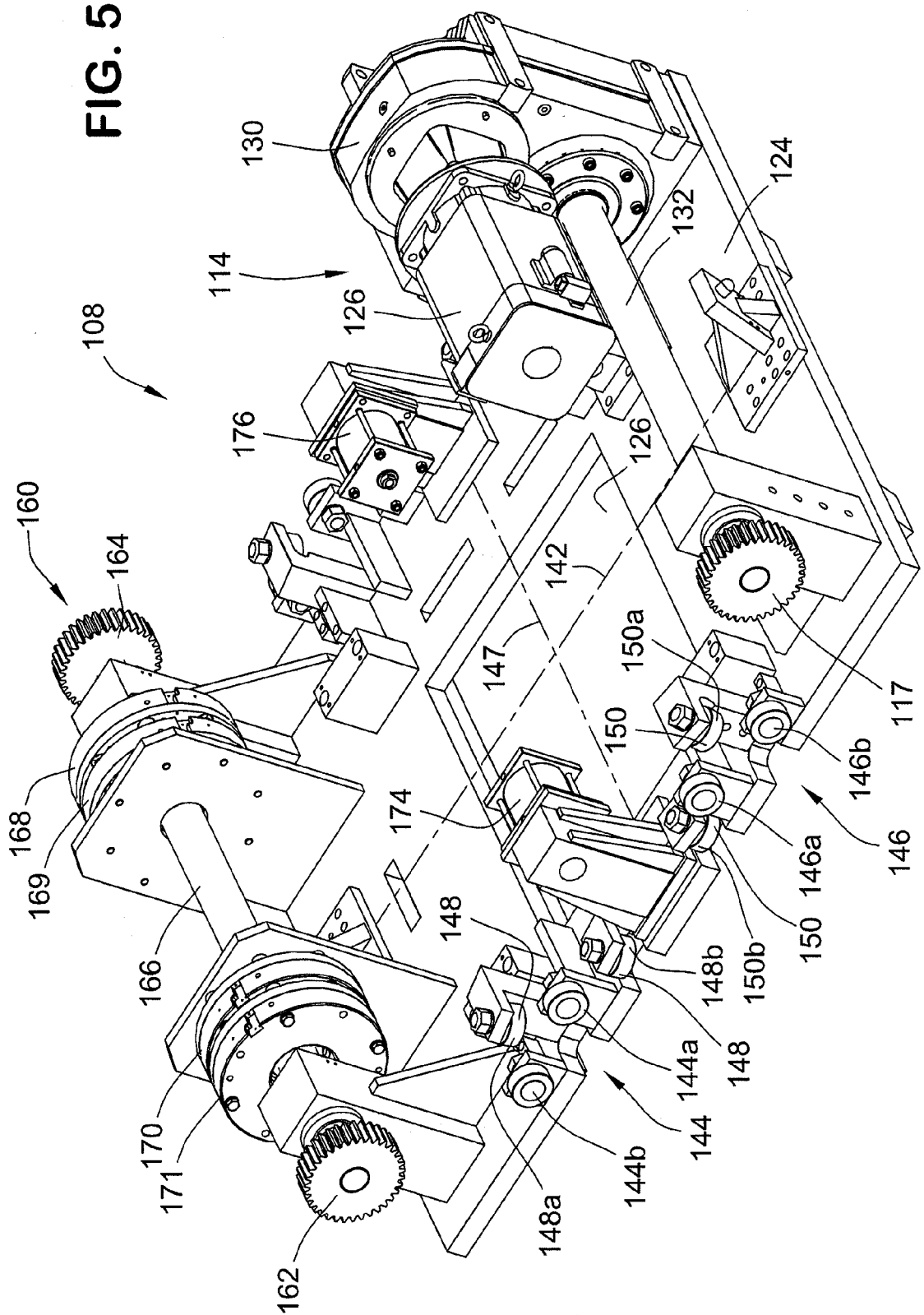
FIGS. 5 and 6 are isometric illustrations of the mounting carriage of the positioning system of FIG. 2.
Figure 6:
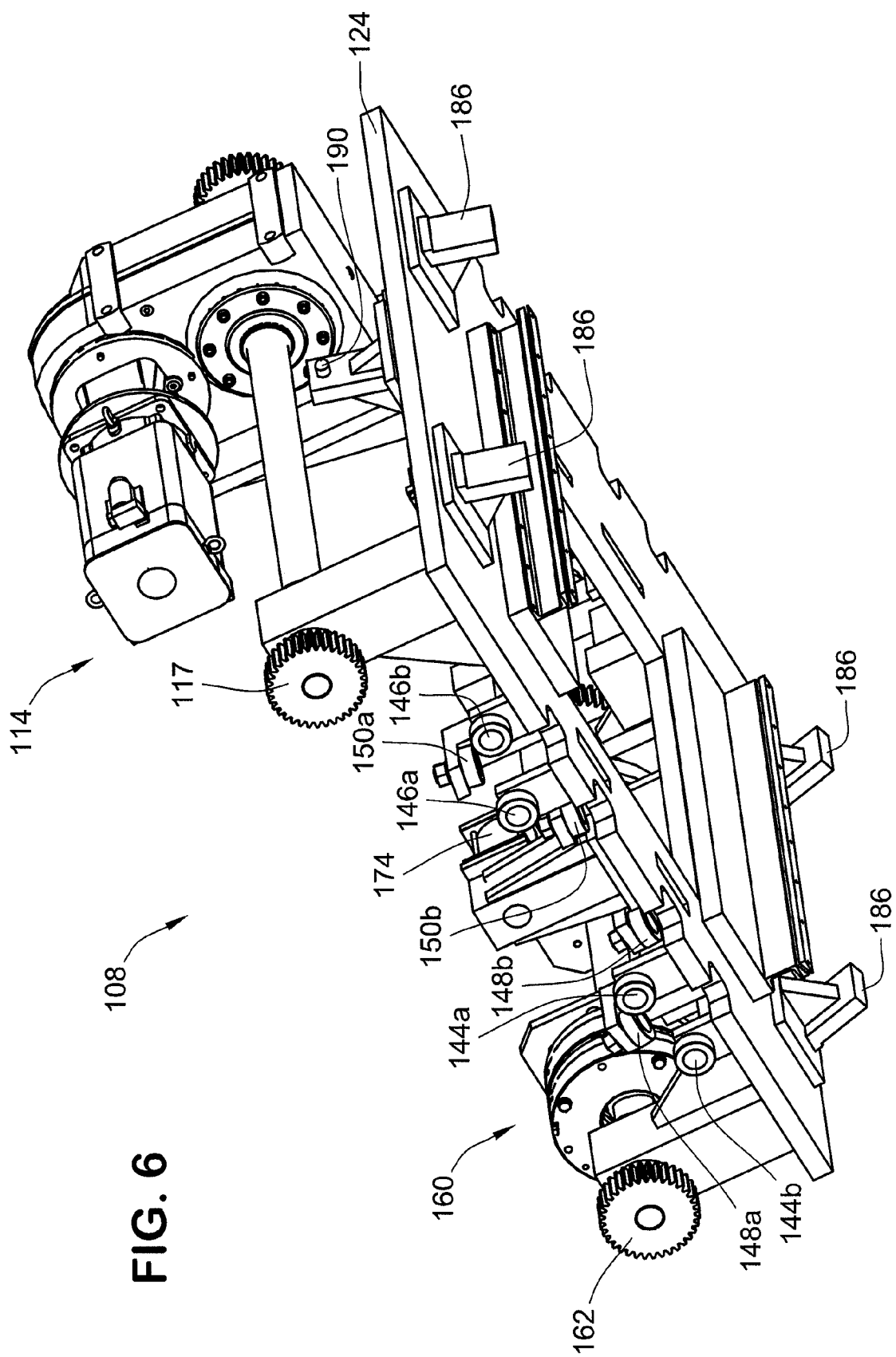

With reference to FIGS. 5 and 6, the mounting carriage 108 is illustrated. The mounting carriage generally includes a frame 124 to which the rest of the mounting carriage components are mounted. The frame 124 generally defines a proton beam nozzle passage 126 through which the proton beam nozzle 102 (see FIG. 1) passes when mounted to the mounting carriage 108.

The mounting carriage, as indicated previously, includes a precision drive arrangement 114 that operably drives the mounting carriage 108 along the drive track arrangements 110, 112. The drive arrangement provides for 50 micron positioning along the carriage guide path 113. The drive arrangement includes a drive motor 126 that drives pinion gear 117 and pinion gear 128 (see FIG. 4), which operably engage the teeth of the gear racks of drive track arrangements 110, 112 to move the mounting carriage 108 along the carriage guide path 113. The drive arrangement 114 also includes a gear train 130 operably positioned between the pinion gears 117, 128. The gear train 130 is a gear reduction gear train.

The drive arrangement 114 of the illustrated embodiment is carried on the mounting carriage 108 such that as the mounting carriage 108 moves along the carriage guide path 113, the drive arrangement 114 is also moved along the carriage guide path 113.

The drive motor 126 is preferably an electronically operated servo motor to provide precise control of the mounting carriage 108. However, other drive motors could be used, such as pneumatic, hydraulic, etc. while remaining within the scope of the present invention.

The two pinion gears 117, 128 are operably coupled to one another for uniform rotation by a pinion gear coupling shaft 132. By using a pair of pinion gears 117, 128, the drive arrangement 114 provides a two point drive arrangement where the first pinion gear 117 operably engages drive track arrangement 110 and the second pinion gear 128 engages drive track arrangement 112.

With reference to FIGS. 3 and 5, for guiding movement of the mooting carriage 108 relative to the drive track arrangements 110, 112 and along the carriage guide path 113, the mounting carriage includes a plurality of cam followers. As the mounting carriage 108 generally interacts with the two drive track arrangements 110, 112 in similar fashion, the mounting carriage 108 is generally symmetric about axis 142 with respect to components that interact with the drive track arrangements 110, 112.

One set of components include the various cam followers that interact with the drive track arrangements 110, 112 to direct the movement of the mounting carriage 108. More particularly, each side of the mounting carriage 108 includes two pairs of guide path cam rollers 144, 146 that each include upper cam rollers 144a, 146a and lower cam rollers 144b, 146b, respectively. The pairs of guide path cam rollers 144, 146 are spaced apart from one another along the guide path so as to improve the stability of the mounting carriage 108 within the cam tracks and to prevent titling along an axis 147 that is generally parallel to the axes of rotation of the cam rollers 144a, 144b, 146a, 146b.

The upper cam rollers 144a, 146a interact with and ride on the upper cam surface 120 of the cam track 118. The lower cam rollers 144b, 146b interact with and ride on the lower cam surface 122 of the cam track 118. In a preferred embodiment, the cam rollers 144a, 146a and 144b, 146b are preloaded against the upper and lower cam surfaces 120, 122 to prevent any clearance from occurring therebetween. Further, the cam rollers 144a, 144b, 146a, 146b are operably coupled to the frame 124 such that their relative positions can be adjusted to calibrate the position of the mounting carriage 108 relative to the drive track arrangements 110, 112. The axes of rotation of cam rollers 144, 146 are preferably substantially positioned on carriage guide path 113.

The mounting carriage 108 includes two additional sets of cam rollers on each side of axis 142 that interact with the drive track arrangements 110, 112. More particularly, each side of the mounting carriage 108 includes two pairs of lateral cam rollers 148, 150. Each pair of lateral cam rollers 148, 150 includes upper cam rollers 148a, 150a and lower cam rollers 148b, 150b, respectively. The lateral cam rollers 148, 150 are used to laterally position the mounting carriage 108 between the support frames 106, 107. These lateral cam rollers 148, 150 ride on the inner lateral face of the drive track arrangements 110, 112 (see e.g. inner face 152 illustrated in FIGS. 4 and 7). The inner lateral faces 152 face inward toward one another. In a preferred embodiment, the upper lateral cam rollers 148a, 150 contact a portion of inner face 152 radially outward from cam track 118 while the lower lateral cam rollers 148b, 150b contact a portion of inner face 152 radially inward from the cam track 118.

The axes of rotation of the lateral cam rollers 148, 150 are prefer canted relative to frame 124 such that the axis of rotation of the lateral cam rollers 48 are generally perpendicular to the tangent of the carriage guide path 113 so as to limit any friction or binding between the cam rollers 148, 150 and inner face 152.

These cam rollers 148, 150 are laterally adjustable toward and away from the inner face of their corresponding drive track arrangement 110, 112. The position of these cam rollers 148, 150 provides fine adjustment for calibrating the lateral position of the mounting carriage 109. Further, the tolerance between the cam followers 148, 150 that interact with the drive track arrangement 110 and the cam followers that interact with drive track arrangement 112 is less than two millimeters, more preferably less than one and on-half millimeters.

The mounting carriage 108 further includes an independent braking system 160. The independent braking system 160 of the illustrated embodiment includes a two point braking arrangement and includes a pair of pinion gears 162, 164 that operably engage the gear racks of the drive track arrangements 110, 112, respectively.

The pinion gears 162, 164 are operably coupled to one another by brake shaft 166 for coordinated braking Four independent brakes 168-171 lock the brake shaft 166, and consequently pinion gears 162, 164 relative to frame 124 of the mounting carriage 108 to prevent movement of the mounting carriage 108 along the carriage guide path 113. In a preferred embodiment, each of the four brakes 168-171 operates independently such that if any brake fails, the other brakes remain working.

Further, the brakes are transitionable between a free state in which the mounting carriage 108 is permitted to move along the carriage guide path 113 and a braking state in which the mounting carriage is prevented from moving along the carriage guide path 113.

The mounting carriage 108 additionally includes a fail safe locking system that includes first and second spring loaded shot pin locks 174, 176. Each shot pin locks 174, 176 cooperates with a corresponding locking aperture array formed by the drive track arrangements 110, 112. The locking aperture arrays are a plurality of angularly spaced apart apertures 178 or cavities formed by the drive track arrangements 110, 112.

The shot pin locks 174, 176 include a spring loaded pin (not shown) that engage (i.e. are received in) individual ones of apertures 178 to provide a positive lock preventing movement of the mounting carriage 108 relative to the drive track arrangements 110, 112. The fail safe locking system is "fail safe" because if power or control of the mounting carriage 108 is lost, the shot pin locks 174, 176 will spring drive their respective pins into engagement with one of the apertures to prevent further movement of the mounting carriage 108. In some embodiments, even when a control failure has not occurred, the fail safe locking system may be used while performing radiotherapy treatments to prevent any problems or reduce any movement of the attached proton beam nozzle should control be lost during a treatment.

Figure 7:
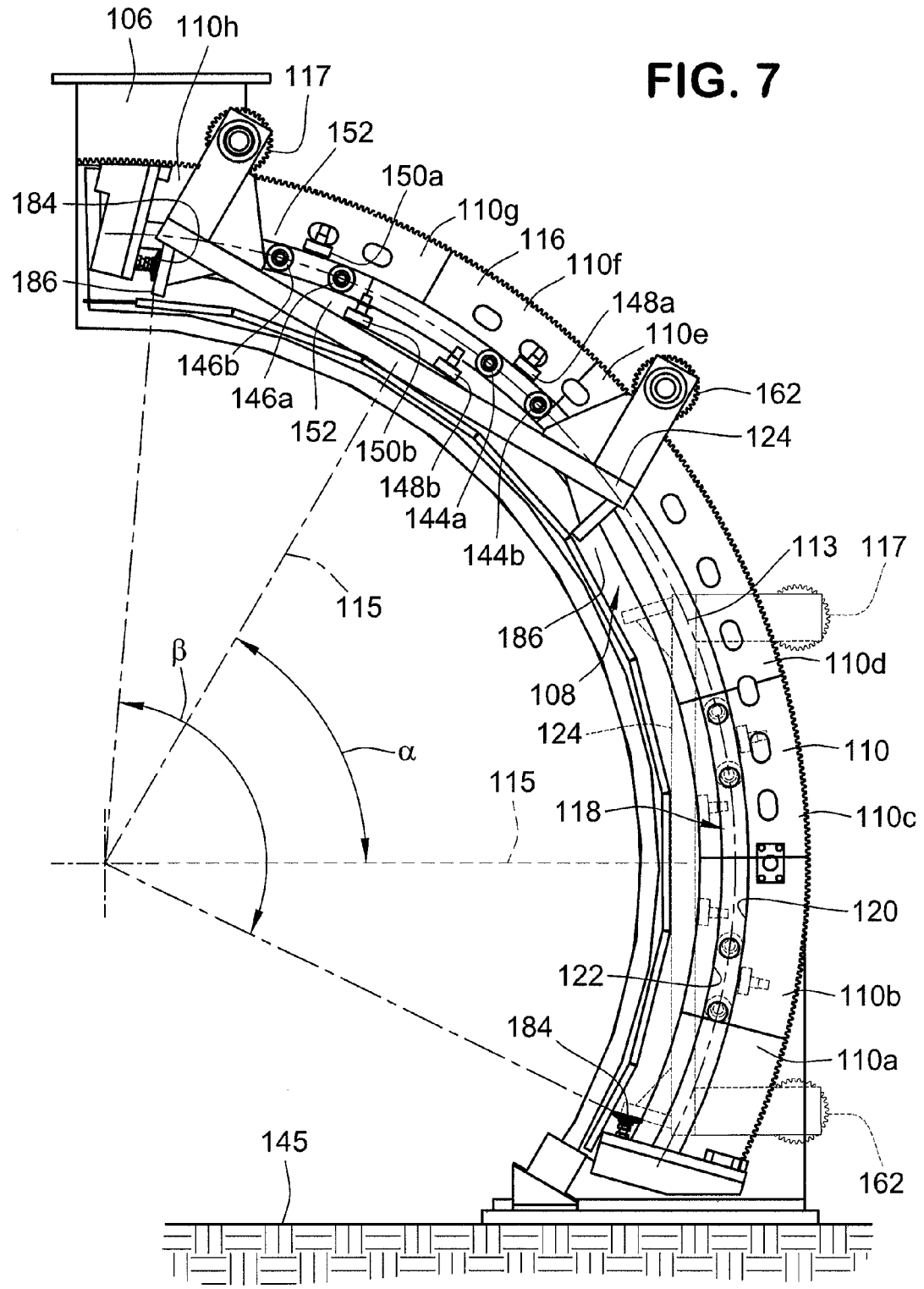
FIG. 7 is a partial side view, similar to FIG. 3, illustrating the various positions of the mounting carriage along the guide path defined by the support frames.

As illustrated in FIGS. 4, 6 and 7, the positioning system 104 includes upper and lower carriage stop assemblies 180, 182 for precisely locating the mounting carriage in predetermined locations. These two predetermined locations for this embodiment position the frame 124 such that the proton beam axis 115 is either horizontal (corresponding to stop assembly 182) or 60 degrees from horizontal (corresponding stop assembly 180). Thus, in this embodiment, the mounting carriage 108 is configured such that it may only travel 60 degrees along the carriage guide path 113 (illustrated as angle α), however the actual drive track arrangements 110, 112 are provided with a greater angular degree as illustrated by angle β.

Each carriage stop assembly 180, 182 includes a pair of fine adjustment bumpers 184 against which the mounting carriage 108 abuts when it is in the two predetermined locations. The position of these bumpers 184 can be adjusted so as to provide fine position calibration of the predetermined locations. The mounting carriage 108 includes bumper brackets 186 that abut the bumpers 184 when the mounting carriage 108 is located at the predetermined locations. The predetermined locations may be referred to "generally predetermined locations" because of the ability to adjust the actual locations by adjusting the position of bumpers 184. Alternatively, the position of brackets 186 could be adjusted.

The carriage stop assemblies also include alignment targets 188 that cooperate with corresponding alignment quills 190 of the mounting carriage 108. The alignment targets 188 of the illustrated embodiment include an aperture 192 that receive the alignment quills 190 when the mounting carriage is properly aligned and in the desired predetermined locations. The alignment targets 188 may also include sensors that can send feedback back to the controller controlling the position of the mounting carriage 108.

While it is desired to use the carriage stop assemblies 180, 182 when performing radiotherapy treatment, other embodiments may position the mounting carriage 108 anywhere in-between the two substantially predetermined positions established by the carriage stop assemblies 180, 182. This is effectuated by the very precise positioning of the mounting carriage 108 provided by drive arrangement 114. More particularly, the mounting carriage 108 is provided with 50 micron positioning accuracy along the carriage guide path 113.

The positioning system 104 further includes a roller shade cover 194 that forms a curtain protecting the majority of the mounting carriage 108 and the proton beam nozzle 102 from exposure to the room in which the radiotherapy treatment is occurring. The shade cover 194 travels along cover tracks 196. The shade cover 194 is drawn from and retracted into a pair of roll-top canisters 198. More particularly, the shade cover 194 is operably coupled to the mounting carriage 108 such that as the mounting carriage moves in one direction more of the shade cover 194 is drawn from one of the canisters 198 and more of the shade cover is retracted into the other one of the canisters 198.

The support frames 106, 107 are typically formed from plate metal welded together to form hollow members. The hollow members may ultimately be filled with concrete or other material to provide additional rigidity and strength. Top and bottom tie plates 200 couple the ends of the support frames 106, 107 to prevent the two devices from pulling laterally apart.

Figure 8:
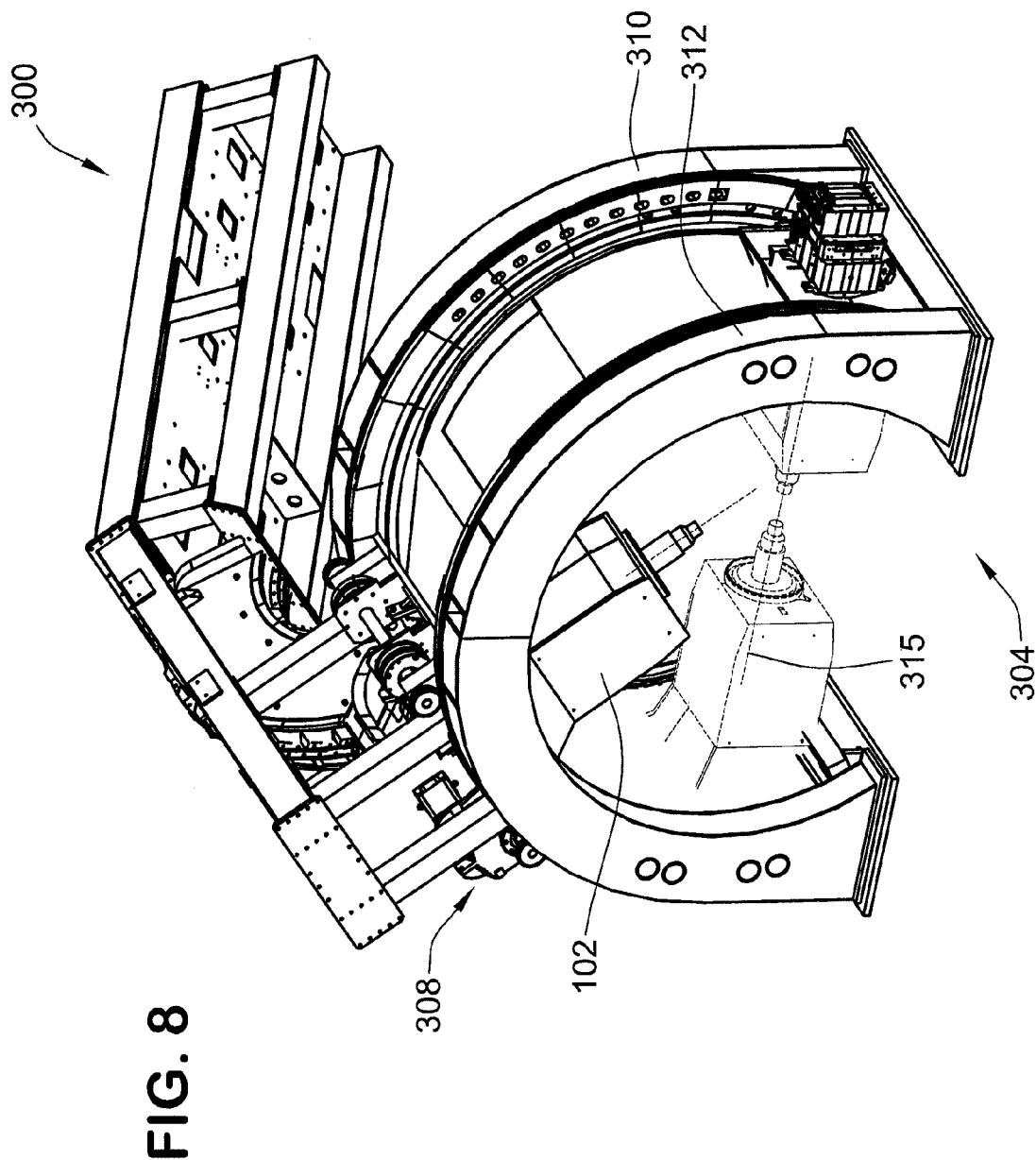
FIG. 8 is a perspective illustration of a second embodiment of a radiotherapy treatment system according to the teachings of the present invention.

Another embodiment of a radiotherapy treatment system 300 is illustrated in FIG. 8. This radiotherapy treatment system 300 is substantially similar to the previous embodiment and only those differences that are present in this embodiment, which may or may not be incorporated into the previous embodiment will be discussed below.

The primary difference in this radiotherapy treatment system is that the positioning system 304 of this embodiment permits increased positioning of the proton beam nozzle 102. More particularly, the position of the proton beam nozzle 102 may be adjusted an entire 180 degrees between opposing horizontal orientations. Thus, this embodiment allows for travel beyond the 60 degrees of travel of the previous embodiment. However, as the travel is substantially limited to 180 degrees, the travel is typically limited below 200 degrees. More particularly, in a first orientation the proton beam nozzle 102 is aligned such that the proton beam is horizontal and extends from the proton beam nozzle 102 towards the right of the page. In a second orientation, the proton beam nozzle 102 has been rotated 180 degrees such that the proton beam is once again horizontal, but in this orientation, the proton beam extends towards the left side of the page. These two end positions are predetermined positions that are similar to the predetermined positions discussed above wherein the mounting carriage contacts stop assemblies. Thus, the drive track arrangements 310, 312 of this embodiment define a carriage guide path that provides for movement by the mounting carriage through a large angle.

In one implementation of this embodiment, the mounting carriage 308 incorporates a pair of drive arrangements. Each drive arrangement is substantially identical to drive arrangement 114 described previously. In this configuration, the two drive arrangements may simultaneously or sequentially drive the mounting carriage. When driven sequentially, the mounting carriage will switch the drive assembly when passing over-center, i.e. past the 90 degree point. However, such a configuration is not required.

While the illustrated embodiments are fully mounted above the floor of the radiotherapy room, alternative embodiments could have the systems mounted below or partially below the floor. Further, embodiments, similar to embodiment 300, a portion could be above the floor and another portion could be below the floor. Typically, in this arrangement, half of the system 300 would be above the floor while the other half of the system 300 would be below the floor. This would allow axis 315 to rotate between vertically up to vertically down as well as an intermediate horizontal orientation. This is opposed to the illustrated arrangement where axis 315 rotates between horizontal left and horizontal right orientations with an intermediate vertical down orientation.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A radiotherapy particle emitter positioning device comprising;
    first and second arcuate support frames, each arcuate support frame including a drive track arrangement defining an arcuate carriage guide path;
    a mounting carriage supported by the support frames, the mounting carriage connectable to the drive track arrangements and moveable along the carriage guide path;
    the mounting carriage including a drive arrangement engaging the drive track arrangements for driving the mounting carriage along the drive track arrangements; and
    wherein the arcuate carriage guide path is defined between two predetermined positions between which the mounting carriage is permitted to travel, the two predetermined positions being spaced apart along the carriage path to provide at least 180 degrees of travel by the mounting carriage along the carriage guide path;
    wherein the first drive track arrangement includes a first gear rack arrangement and a second drive track arrangement includes a second gear rack arrangement; and
    the drive arrangement including a four point drive arrangement including first and second spaced apart pinion gears engaging the first gear rack arrangement and third and fourth pinion gears engaging the second gear rack arrangement, the first and third pinion gears operably coupled for coordinated driving of the mounting carriage and the second and fourth pinion gears operably coupled for coordinated driving of the mounting carriage.

2. The positioning device of claim 1, wherein the two predetermined positions are spaced apart along the carriage guide path to provide less than 200 degrees of travel.

3. The positioning device of claim 1, wherein the two predetermined positions are spaced apart along the carriage guide path to provide a first orientation of the radiotherapy particle emitter such that a radiotherapy particle beam emitted therefrom is oriented horizontally in a first direction, and a second orientation of the radiotherapy particle emitter such that the radiotherapy particle beam emitted therefrom is oriented horizontally in a second direction opposite the first direction.

4. The position device of claim 1, wherein the two predetermined positions are spaced apart along the carriage guide path to provide a first orientation of the radiotherapy particle emitter such that a radiotherapy particle beam emitted therefrom is oriented in a first direction, and a second orientation of the radiotherapy particle emitter such that the radiotherapy particle beam emitted therefrom is oriented in a second direction opposite the first direction.

5. The position device of claim 4, wherein the mounting carriage positions the radiotherapy particle emitter at a plurality of positions between the two predetermined positions such that a radiotherapy particle beam emitted therefrom is oriented at an angle relative to the first direction.

* * * * *